(12) United States Patent
Bauer et al.

(10) Patent No.: US 7,165,441 B2
(45) Date of Patent: Jan. 23, 2007

(54) SENSOR MODULE HAVING A SENSOR ELEMENT SURROUNDED BY A HEATING ELEMENT

(75) Inventors: Michael Bauer, Tuebingen (DE); Isolde Simon, Kusterdingen (DE); Michael Arndt, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 205 days.

(21) Appl. No.: 10/489,904

(22) PCT Filed: Aug. 27, 2002

(86) PCT No.: PCT/DE02/03129

§ 371 (c)(1), (2), (4) Date: Sep. 20, 2004

(87) PCT Pub. No.: WO03/027654

PCT Pub. Date: Apr. 3, 2003

(65) Prior Publication Data

US 2005/0028580 A1     Feb. 10, 2005

(30) Foreign Application Priority Data

Sep. 20, 2001   (DE) ................. 101 46 321

(51) Int. Cl.
    *G01N 25/18* (2006.01)
(52) U.S. Cl. .................................... 73/25.03
(58) Field of Classification Search ............... 73/25.03
    See application file for complete search history.

(56) References Cited

U.S. PATENT DOCUMENTS

| | | | |
|---|---|---|---|
| 4,332,157 A * | 6/1982 | Zemel et al. | 73/204.16 |
| 4,682,503 A * | 7/1987 | Higashi et al. | 73/755 |
| 4,719,441 A * | 1/1988 | Horn | 338/20 |
| 4,885,937 A * | 12/1989 | Tanaka et al. | 73/170.12 |
| 4,902,138 A * | 2/1990 | Goeldner et al. | 374/44 |
| 4,928,513 A * | 5/1990 | Sugihara et al. | 73/25.03 |
| 4,944,035 A * | 7/1990 | Aagardl et al. | 702/136 |
| 4,966,037 A * | 10/1990 | Sumner et al. | 73/204.26 |
| 5,038,304 A * | 8/1991 | Bonne | 702/99 |
| 5,044,764 A | 9/1991 | Aoki et al. | |
| 5,295,389 A * | 3/1994 | Nagata et al. | 73/25.03 |
| 5,303,167 A | 4/1994 | Bonne | |
| 5,377,527 A * | 1/1995 | Kamiunten | 73/25.03 |
| 5,464,966 A * | 11/1995 | Gaitan et al. | 219/544 |
| 5,515,714 A | 5/1996 | Sultan et al. | |
| 5,597,957 A * | 1/1997 | Schieferdecker et al. | 73/755 |
| 5,756,878 A * | 5/1998 | Muto et al. | 73/25.03 |
| 6,290,388 B1 * | 9/2001 | Saul et al. | 374/44 |
| 6,406,181 B1 * | 6/2002 | Mueller et al. | 374/185 |

(Continued)

FOREIGN PATENT DOCUMENTS

DE   37 11 511   6/1988

(Continued)

*Primary Examiner*—Hezron Williams
*Assistant Examiner*—John Fitzgerald
(74) *Attorney, Agent, or Firm*—Kenyon & Kenyon LLP

(57) ABSTRACT

A sensor module having a heating structure and a sensor element is described. The heating structure surrounds the sensor element so that heat dissipation through a frame is largely prevented. This yields a greater measuring accuracy of the sensor module. In particular, interfering influences due to a temperature dissipation through the mount frame are thereby prevented.

13 Claims, 3 Drawing Sheets

U.S. PATENT DOCUMENTS 6,470,742 B1 * 10/2002 Yamakawa et al. ...... 73/204.26
6,684,694 B2 * 2/2004 Fujiwara et al. ......... 73/204.26
2002/0121137 A1 * 9/2002 Fujiwara et al. ......... 73/204.26

FOREIGN PATENT DOCUMENTS

| DE | 3923595 C | * | 12/1990 |
| DE | 196 24 683 | | 10/1997 |
| DE | 196 34 690 | | 2/1998 |
| DE | 299 07 566 | | 9/1999 |
| DE | 199 63 966 | | 7/2001 |
| DE | 19963966 A1 | * | 7/2001 |
| EP | 0 724 151 | | 7/1996 |
| WO | 00 70333 | | 11/2000 |

* cited by examiner

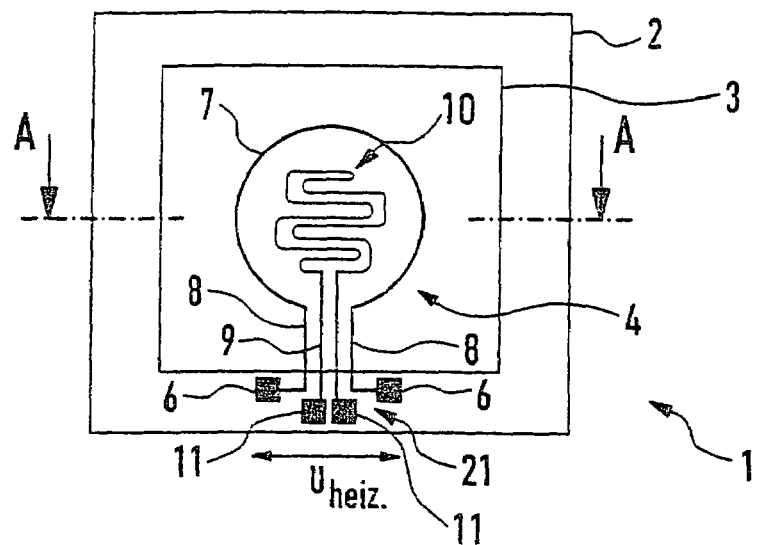
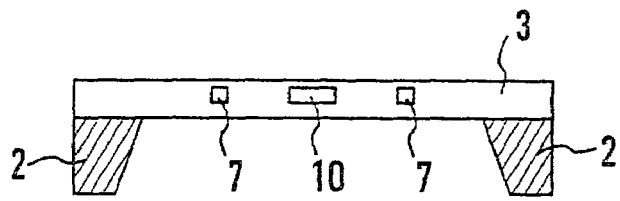
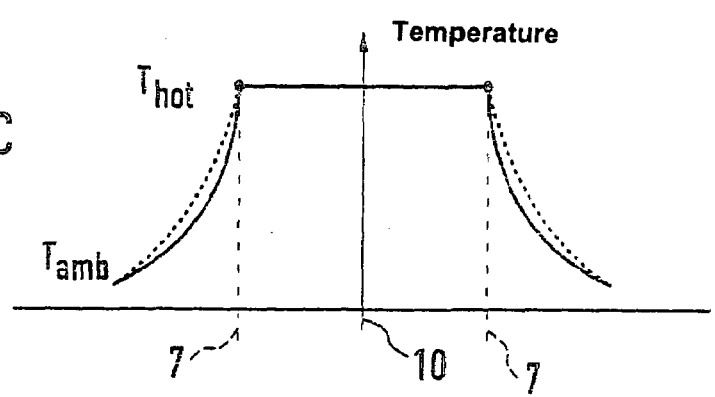

SENSOR MODULE HAVING A SENSOR ELEMENT SURROUNDED BY A HEATING ELEMENT

FIELD OF THE INVENTION

The present invention relates to a sensor module and a method for measuring the conductivity of a gas using a sensor module.

Sensor modules are used in various technical fields, in particular for measuring the thermal conductivity of a gas for gas analysis. To determine the thermal conductivity of a gas, a heated body is used, its heat losses being determined mostly by dissipation of heat to the surrounding gas. Consequently, the heating power needed by the heated body to maintain a constant temperature is a direct measure of the thermal conductivity of the surrounding gas.

BACKGROUND INFORMATION

Possible heated bodies include heater wires, structured heater resistors on films, and heater resistors on microstructured dielectric diaphragms. The dielectric diaphragms which are produced by silicon micromechanics processes are becoming increasingly important because of their rapid response time, small size, and batch processability. Large numbers of thermal conductivity sensors will be needed in the future for use in hydrogen-powered vehicles, for example. Hydrogen has a very high thermal conductivity in comparison with air and therefore is readily detectable using a thermal conductivity sensor.

For example, the change in the heater resistance under the influence of the thermal conductivity of the surrounding gas is analyzed as the measuring signal for determining the thermal conductivity of a gas, with the heating power being kept constant. Another method of measurement involves regulating the heater resistance at a constant level, i.e., at a constant temperature, and analyzing the power required to do so as the signal. Based on the measurement of the change in resistance or of the controlled variable of power, it is possible to calculate the thermal conductivity of the gas.

One problem in analyzing such sensor modules, however, is that the sensor signal of the known thermal conductivity sensors depends not only on the thermal conductivity of the gas surrounding the heated body, but also on the heat dissipation through the mount of the heated body on the thermal radiation. The heat losses, which are undesirable for the application and are attributed to dissipation of heat through the mount for the heated body and due to radiation are minimized by using materials that are well insulated thermally and low temperatures at which the thermal conductivity sensors are operated.

It is furthermore known that it is possible to provide a second heated body which is identical to the first heated body and is acted upon by a reference gas. By comparing the signals of the two heated bodies, the sensitivity of the thermal conductivity sensor may be improved using a bridge circuit, for example. Such a sensor design is often used for laboratory measurements, but it seems too complicated for a small, compact and sturdy sensor module such as that needed for use in the automotive industry, for example.

SUMMARY OF THE INVENTION

An object of the present invention is to provide a sensor module which is insensitive to dissipation of heat through the mounts of the heated body.

The object of the present invention is achieved by a sensor module. An important advantage of the sensor module according to the present invention is that a heating element which at least partially surrounds the sensor element is provided. In this way, the sensor element is better protected from dissipation of heat. The sensor element is thus less sensitive to dissipation of heat, which occurs, for example, through the mount of the sensor module. Thus on the whole, the sensitivity of the sensor module is increased so that a reference measurement is no longer necessary.

In a preferred embodiment, the sensor module has a heating element which almost completely surrounds the sensor element. This ensures almost thermal insulation of the sensor element with respect to dissipation of heat through the mount of the sensor module. This achieves almost complete isolation of the sensor element from the dissipation of heat through the mount and further increases the sensitivity of the sensor module.

A preferred embodiment of the sensor module has a heating element which is designed in the form of at least two heating structures. Due to the design of two independent heating structures, it is possible to heat the two heating structures independently of one another and thus if necessary balance out an asymmetrical system of the two heating structures with respect to the sensor element through different triggering. It is thus possible in particular to perform a precise calibration of the sensor module and thereby compensate for any inaccuracies in manufacture of the heating element.

A temperature sensor is preferably assigned to each heating structure so that the temperature of each heating structure is independently regulable.

In a simple embodiment of the sensor element, the sensor element is designed as a resistance element. The heating element is preferably designed essentially in the form of a ring structure. The form of a ring structure permits a simple form of embodiment of the heating element in which the sensor element may be largely surrounded by the heating element and the sensor element is thereby reliably protected from dissipation of heat.

In another preferred embodiment, the heating element has essentially the form of a rectangular structure. The design of the heating element as a rectangular structure is technologically easy to produce.

In a preferred embodiment of the rectangular structure, one half of the rectangular structure is formed by a heating structure. This makes it possible to compensate for any geometric inaccuracy with respect to a symmetrical position in relation to the sensor element through different triggering of the two heating structures.

A particularly simple sensor module structure is achieved by designing the heating element and the sensor element in two different layers. The method for manufacturing the sensor module, for example, thus becomes more flexible. The two layers may preferably be manufactured of one material which is adapted to the material of the heating element and/or the material of the sensor element. In addition, the two layers may be manufactured separately from one another in a preferred embodiment and then joined together by a bonding method, for example.

Preferably the carrier of the sensor module has a diaphragm and a diaphragm mount. The heating element and the sensor element are positioned on the diaphragm. The diaphragm mount is used for holding the sensor module, e.g., in a suitable housing.

The object of the present invention is also achieved by a method according to the present invention that has the advantage that any inaccuracy in the heating structures may be compensated by the system of two heating structures which are triggerable independently of one another. This improves the measuring accuracy of the sensor module.

DETAILED DESCRIPTION

Figure 1D:
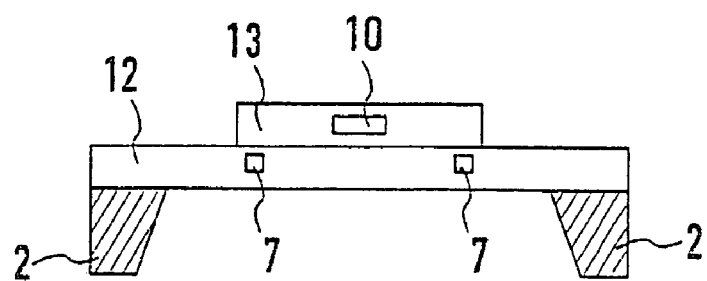
FIG. 1 shows a first embodiment of a sensor module.

FIG. 1A shows a sensor module 1 which is used, for example, for measuring the thermal conductivity of a gas surrounding sensor module 1. Sensor module 1 has a mount frame 2 and a diaphragm 3 attached to mount frame 2. Mount frame 2 and diaphragm 3 are preferably manufactured of a material that is machinable by micromechanical manufacturing methods. Silicon is preferably used to manufacture mount frame 2, and a dielectric material such as silicon oxide or silicon nitride is used to manufacture diaphragm 3. A heating element 4 is applied to diaphragm 3. Heating element 4 has electric terminals 6 designed in the lower region of mount frame 2. Heating element 4 is composed essentially of an annular structure 7 which is electrically connected to terminal faces 6 via connecting lines 8. Annular structure 7 is not completely closed but instead has an opening area 21 through which second connecting lines 9 of a sensor element 10 run from the lower region of mount frame 2 into the center of annular structure 7. Sensor element 10 is connected via second connecting lines 9 to second terminal faces 11 which are provided on mount frame 2.

In the exemplary embodiment depicted here, sensor element 10 is implemented in the form of a second heating element. Sensor element 10 preferably has a wave-form structure which is situated essentially around the midpoint of annular structure 7.

Annular structure 7 is a preferred embodiment of the present invention, but the shape of heating element 4 is not limited to annular structure 7. The shape of heating element 4 is designed so that heating element 4 at least partially surrounds a sensor element 10 and thus dampens or preferably insulates it thermally from mount frame 2. The function of the shape of heating element 4 is to isolate sensor element 10 thermally from mount frame 2 and thus largely prevent any influence on the temperature of the sensor element due to a heat flow over mount frame 2. Instead of the form depicted here, heating element 4 may also have any other type of ring shape or partial ring shape.

Instead of being designed as a second heating element, sensor element 10 may also be designed as a temperature sensor. However, the resistance of sensor element 10 in the embodiment as a second heating element may also be analyzed to determine the temperature within annular structure 7.

FIG. 1B shows a cross section A-A through sensor module 1. This shows clearly the cross-sectional shape of mount frame 2 and the cross-sectional shape of diaphragm 3. In addition, sensor element 10 and heating element 4 are situated in a single layer in this embodiment.

Depending on the application, it may be advantageous for sensor element and heating element 4 to be situated in different layers one above the other. For example, the layer for sensor element 10 may be smaller and may be situated centrally in relation to annular structure 7, for example. The second layer in which sensor element 10 is preferably situated extends only slightly beyond annular structure 7. This provides additional separation between the second layer, in which sensor element 10 is provided, and mount frame 2.

Sensor module 1 according to FIGS. 1A and 1B is preferably used for determining the thermal conductivity of a gas next to diaphragm 3. Various methods of measurement may be used to determine the thermal conductivity.

For example, if sensor element 10 is designed as a second heating element, then the heating power with which sensor element 10 is operated is adjusted in such a way that the same temperature prevails inside annular structure 7 as in the area of annular structure 7 itself. If the heating element is designed as a resistor, then the resistor may also function as a temperature sensor at the same time. Furthermore, additional temperature sensors such as diodes may also be used to measure the temperature beneath annular structure 7.

The thermal conductivity of the gas next to diaphragm 3 may be determined on the basis of the power required to keep the temperature constant. If the gas has a higher thermal conductivity, a greater heating power is necessary to establish the same temperature over sensor element 10 as that on annular structure 7.

If the gas has a lower thermal conductivity, a lower heating power is sufficient for sensor element 10 to establish the same temperature within annular structure 7 as in the area of annular structure 7.

Similar methods of measurement are described for example by Hartmann and Braun, Product Information, Leaflet for the TCS 208 F (3), 1999.

FIG. 1C shows, for example, the temperature distribution on diaphragm 3, where the temperature rises steeply starting from mount frame 2 up to annular structure 7 and is essentially constant within annular structure 7 due to an appropriate regulation of sensor element 10 which is designed as a second heating element. In the area between annular structure 7 and mount frame 2, a slight effect is measured between a high thermal conductivity and a low thermal conductivity of the gas next to diaphragm 3. The temperature distribution for a high thermal conductivity is depicted in FIG. 1C in the form of a solid line and the temperature distribution for a low thermal conductivity is depicted in the form of a dotted line.

FIG. 1D shows an embodiment of sensor module 1 according to the present invention in which heating element 4 and sensor element 10 are situated in different layers. A first layer is depicted as being on mount frame 2 and a second layer 13 as resting on first layer 12. Second layer 13 essentially covers the area delimited by annular structure 7 and has a sensor element 12. First and second layers 12, 13 are preferably made of the same dielectric material which has a low thermal conductivity. Due to the design of the two layers 12, 13 there is an additional isolation of sensor element 10 from a heat flow in the direction of mount frame 2. Furthermore, the design of two separate layers 12, 13 for accommodating heating element 4 and sensor element 10 offers the advantage that the manufacturing methods for heating element 4 and sensor element 10 may be performed separately, and in addition the connecting lines may be designed independently of the shape of heating element 4 and/or the shape of sensor element 10.

Figure 2:
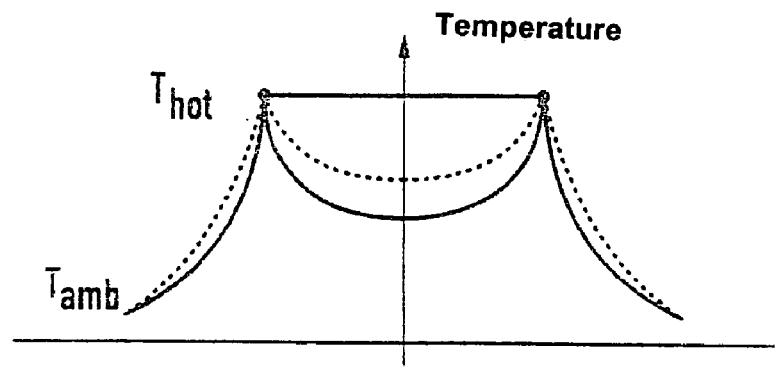
FIG. 2 shows a second embodiment of a sensor module.

FIG. 2 shows a plot of a heat distribution when using sensor module 1 from FIG. 1A and a method of measurement in which sensor element 10 is designed only as a temperature sensor and the temperature inside annular structure 7 is detected using sensor element 10. Depending on the thermal conductivity of the gas next to diaphragm 3, different variations of temperature and different temperatures are measured inside annular structure 7. FIG. 2 shows as a solid line the temperature variation on diaphragm 3 for a high thermal conductivity. The temperature variation for a low thermal conductivity of the gas is shown in the form of a dotted line. In this application, sensor element 10 is designed either only as a temperature sensor or sensor element 10 is additionally designed as a heating element according to the embodiment of FIG. 1A, but is used only as a temperature sensor by resistance measurement. In the methods of measurement according to the temperature distributions in FIG. 1C and FIG. 2, heating element 4 is heated to a predetermined temperature Tj in each case and the power for heating the heating element 4 is readjusted accordingly.

Figure 3:
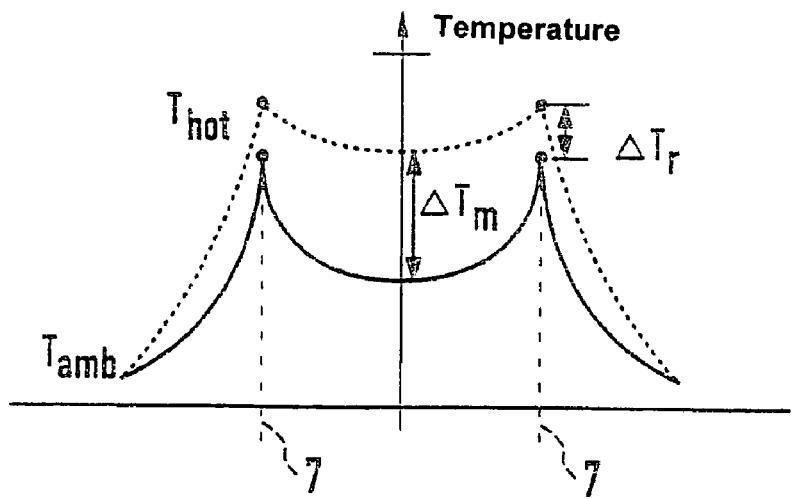
FIG. 3 shows a third embodiment of a sensor module.

FIG. 3 shows the temperature variation in another method of measurement in which heating element 4 is operated at a constant power. In this method of measurement, the temperature values for annular structure 7 are also shifted as a function of the thermal conductivity of the surrounding gas. If the thermal conductivity is high, the result is a temperature distribution such as that shown here in the form of a solid line. When the surrounding gas has a low thermal conductivity, the result is a temperature distribution such as that illustrated in the form of a dotted line. Since heating element 4 is heated at a constant power, the temperature in the area of ring structure 7 also changes. This temperature difference is denoted as ΔTr. Inside of annular structure 7, the temperature also has different values, depending on the thermal conductivity. This temperature difference is denoted as ΔTm at the center of annular structure 7. The thermal conductivities of the gases may also be calculated by known methods, depending on the temperature differences.

Figure 4:
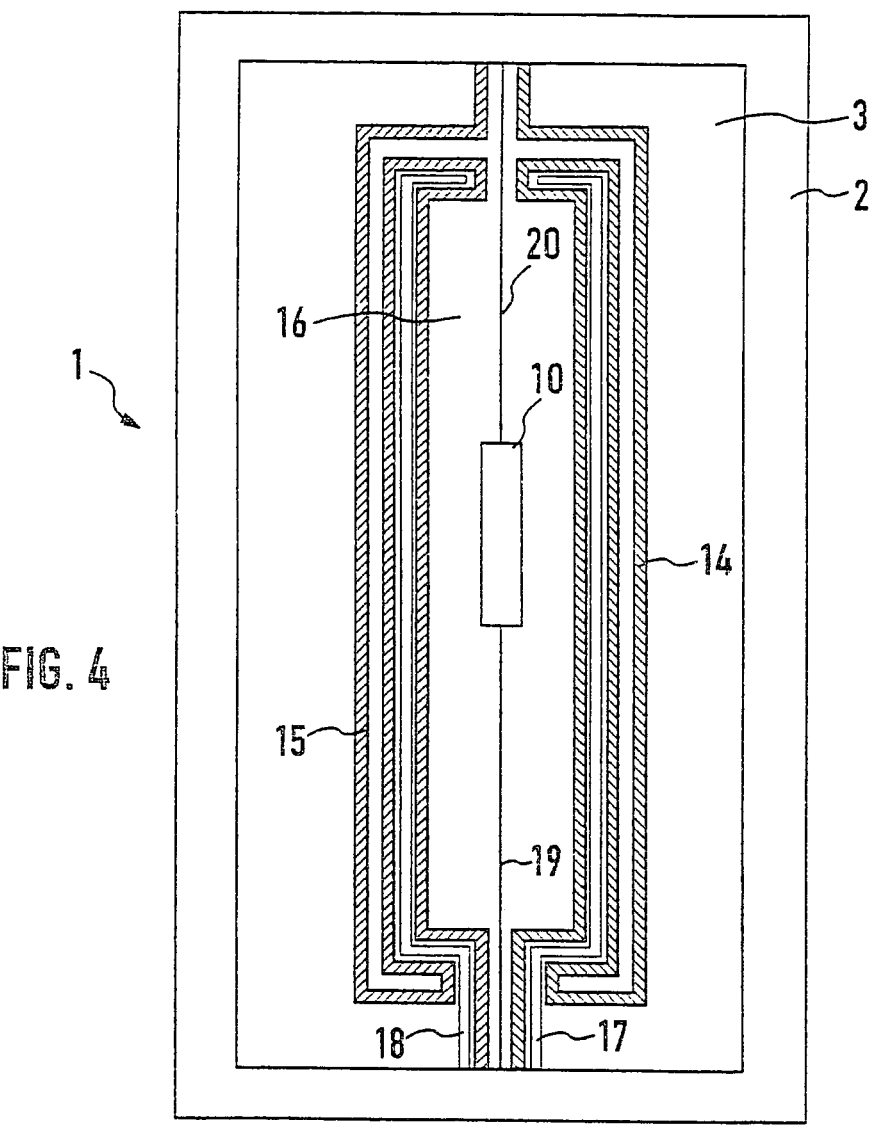
FIG. 4 shows a schematic diagram of a temperature response of a sensor module.

FIG. 4 shows another embodiment of a sensor module 1. In this embodiment, a first and a second heating structure 14, 15 are provided as heating element 4, each bordering half of a border of a rectangular area. The rectangular area bordered by first and second heating structures 14, 15 is a thermal area 16 of diaphragm 3, which is thermally isolated with respect to mount frame 2. Sensor element 10 is situated at the center of thermal area 16 and is implemented in this exemplary embodiment as a heating sensor coil. The heating sensor coil has two connecting lines 19, 20 which are connected to opposite sides of mount frame 2.

First and second heating structures 14, 15 are situated in mirror symmetry to one another and are designed identically. First heating structure 14 has a line structure including a plurality of line sections, individual sides of the border of the rectangular area being assigned a plurality of parallel line sections. The line sections are preferably designed as straight lines. The individual line sections are interconnected in the form of a single line. The individual line sections are spaced a predetermined distance apart and are . . . situated in lateral surfaces of a rectangle. The upper and lower lateral surfaces of the rectangle are bordered one half by the first line section and one half by the second line section. This yields an essentially semirectangular wave-form structure. In the preferred embodiment, a plurality of line sections are situated between thermal area 16 and mount frame 2. This permits an improved thermal isolation of thermal area 16 from mount frame 2. A first temperature sensor 17 is preferably provided between an innermost line section and a second line section adjacent to the innermost line section; this temperature sensor is designed essentially in the form of a closed line and in the form of the semirectangular waveform structure of first heating structure 14. First temperature sensor 17 is connected to the lower lateral edge of mount frame 2. A first end of first heating structure 14 is connected to the upper lateral part of mount frame 2 and the second end of first heating structure 14 is connected to the lower lateral part of mount frame 2.

Second heating structure 15 is designed in mirror symmetry with first heating structure 14 and likewise has a second temperature sensor 18 in mirror symmetry with first temperature sensor 17.

FIG. 4 shows a preferred embodiment of heating element 4, where the shape of the first and second heating structures 14, 15 may also be in the form of an annular structure. One advantage of first and second heating structures 14, 15 is that a better thermal isolation between thermal area 16 and mount frame 2 is achieved due to multiple line sections situated side-by-side, and furthermore, a symmetrical temperature distribution in the area of thermal area 16 is achievable through the system of two independently regulable heating structures 14, 15. For example, if first and second heating structures 14, 15 are applied to diaphragm 3 at different distances from the central position of sensor element 10, then this deviation in the geometric configuration is compensatable through a different power control, so that sensor element 10 is exposed to essentially the same temperature distribution in all directions.

Figure 5:
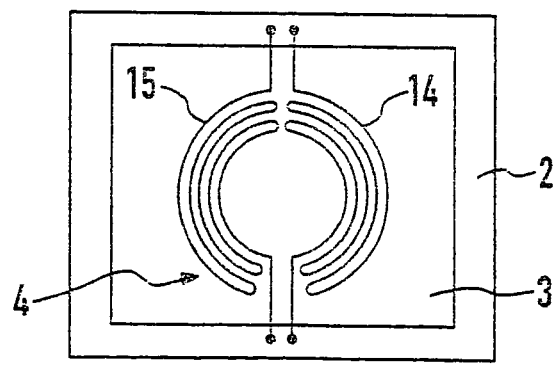
FIG. 5 shows a fourth embodiment of a sensor module.

FIG. 5 shows a ring-shaped heating element having two heating structures which have a plurality of line sections situated side-by-side.

According to the exemplary embodiment in FIG. 1, sensor element 10 may be designed in the form of a heating element and/or temperature element or it may be designed only in the form of a temperature element with which the temperature is measured. It is also possible for sensor element 10 and first and second heating structures 14, 15 to be provided in different layers according to the exemplary in embodiment in FIG. 1. Heating element 4 and heating structures 14, 15 are implemented in the form of printed conductors, for example.

For different triggering of first and second heating structures 14, 15, a suitable control unit is provided, the power of first and second heating structures 14, 15 being adjustable at different levels by this control unit. Improved measuring conditions are made possible in this way.

What is claimed is:

1. A sensor module, comprising:
    a heating element;
    a sensor element; and
    a carrier to which is applied the heating element and the sensor element, wherein:
        the heating element is for adjusting a temperature of the carrier,
        the sensor element is for determining the temperature of the carrier,
        the heating element at least partially surrounds the sensor element, and
        the heating element includes at least two heating structures.

2. The sensor module as recited in claim 1, wherein:
    the heating element delimits the sensor element substantially completely.

3. The sensor module as recited in claim 1, wherein:
    the heating element delimits the sensor element completely.

4. The sensor module as recited in claim 1, wherein:
a power of the at least two heating structures is separately regulable.

5. The sensor module as recited in claim 1, further comprising:
a temperature sensor for each of the at least two heating structures.

6. The sensor module as recited in claim 1, wherein:
the sensor element includes a heating element.

7. The sensor module as recited in claim 1, wherein:
the carrier includes a first layer and a second layer,
the heating element is situated in the first layer, and
the sensor element is situated in the second layer.

8. The sensor module as recited in claim 1, wherein:
the carrier includes a diaphragm and a diaphragm mount, and
the heating element and the sensor element are situated on the diaphragm.

9. The sensor module as recited in claim 1, wherein:
the heating element includes an at least partial ring structure.

10. The sensor module as recited in claim 9, wherein:
the heating element includes a ring structure.

11. The sensor module as recited in claim 1, wherein:
the heating element includes a rectangular structure.

12. The sensor module as recited in claim 11, wherein:
each side of the rectangular structure is formed by a heating structure.

13. A method for measuring a conductivity of a gas using a sensor module including a heating element, a sensor element; and a carrier to which is applied the heating element and the sensor element , the heating element being capable of adjusting a temperature of the carrier, the sensor element capable of determining the temperature of the carrier, the heating element at least partially surrounding the sensor element, the heating element including a rectangular structure, and each side of the rectangular structure being formed by a heating structure, the method comprising:
setting, via two of the heating structures, one of a predetermined temperature and a heating power to be generated by at least one of the two heating structures;
detecting, via the sensor element, at least one of a temperature and a heating power of the sensor element required to set a temperature prevailing on the two heating structures;
deriving information regarding the conductivity of the gas from the at least one of the temperature and the heating power of the sensor element; and
regulating a heating power of the two heating structures independently of one another.

* * * * *